United States Patent [19]
Masuo et al.

[11] Patent Number: 5,817,031
[45] Date of Patent: Oct. 6, 1998

[54] IMPEDANCE MEASURING DEVICE AND A HEALTH MANAGEMENT DEVICE USING THE SAME

[75] Inventors: Yoshihisa Masuo; Soichi Okuhara; Manabu Yoshimura, all of Kyoto, Japan

[73] Assignee: OMRON Corporation, Kyoto, Japan

[21] Appl. No.: 568,765

[22] Filed: Dec. 7, 1995

[30] Foreign Application Priority Data

Dec. 7, 1994 [JP] Japan .................................. 6-303323

[51] Int. Cl.⁶ ...................................................... A61B 5/05
[52] U.S. Cl. ............................................................ 600/547
[58] Field of Search .................................. 128/639, 734, 128/696; 600/372, 547, 548

[56] References Cited

U.S. PATENT DOCUMENTS

| | | | |
|---|---|---|---|
| 3,602,215 | 8/1971 | Parnell ..................................... | 128/696 |
| 4,947,862 | 8/1990 | Kelly ....................................... | 128/734 |
| 5,063,937 | 11/1991 | Ezenwa et al. ...................... | 128/734 X |
| 5,197,479 | 3/1993 | Hubelbank et al. ................... | 128/696 |
| 5,372,141 | 12/1994 | Gallup et al. .......................... | 128/734 |
| 5,579,782 | 12/1996 | Masuo .................................... | 128/734 |

FOREIGN PATENT DOCUMENTS

| 0 026 796 | 4/1981 | European Pat. Off. . |
|---|---|---|
| 0 343 928 | 11/1989 | European Pat. Off. . |

OTHER PUBLICATIONS

Elektrotechnik & Informationstechnik, vol. 108, No. 3, 1991:96–113, Wein (AT), XP 000225411, G. Biegelmeir et al., "Neue Messugen des Korperwiderstands lebender Menschen mit Wechselstrom 50Hz sowie mit hoheren Frequenzen und mit Gleichstrom", figure 10, tables 11, Z–12.

Patent Abstracts of Japan, vol. 950, No. 001, and JP–A–07 012635 (Ya Man Ltd), 17 Jan. 1995, abstract only.

*Primary Examiner*—Francis Jaworski
*Attorney, Agent, or Firm*—Morrison & Foerster LLP

[57] ABSTRACT

A device for providing data as a guide to health management which is capable of highly accurate measurements measures various characteristics of the body of a subject by electrical measurements of the subject while he or she is grasping handgrips with which the device is equipped. Once measurement has begun, the impedance variability measured by the device is calculated at every sampling period, and if the value of this variability is continuously less than a predetermined amount over a number of samplings, it is concluded that the electrodes which apply a fixed current and the electrodes which detect voltage are making good contact with the subject's hands.

10 Claims, 16 Drawing Sheets

SHOULDERS' WIDTH

SHOULDERS' WIDTH

FIG. 10
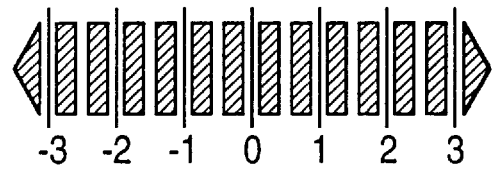
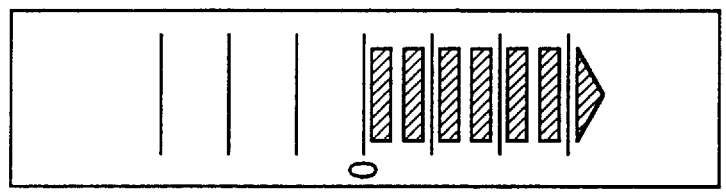
FIG. 11(a)
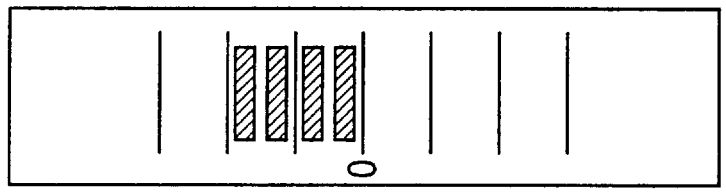
FIG. 11(b)
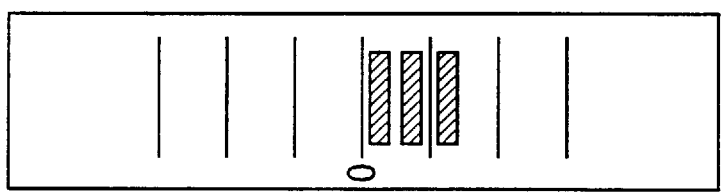
FIG. 11(c)
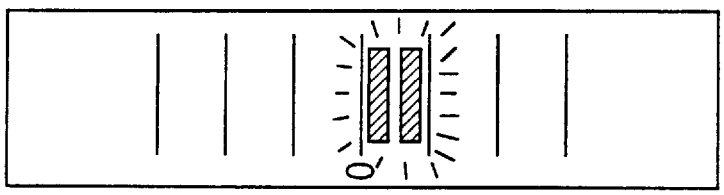
FIG. 11(d)

1

IMPEDANCE MEASURING DEVICE AND A HEALTH MANAGEMENT DEVICE USING THE SAME

FIELD OF THE INVENTION

This invention concerns a device to measure the electrical impedance of the body and a device to provide data as a guide to health management which employs such an impedance measurement device, and which provides guidance pertaining to health management, such as the content of fat in a human body.

BACKGROUND OF THE INVENTION

This application is related to our prior and co-pending U.S. application Ser. No. 08/288,719 filed Aug. 12, 1994, issued Dec. 1, 1996, as U.S. Pat. No. 5,579,782, for a device to provide data as a guide to health management which measures such variables as body fat ratio. The disclosure of U.S. Pat. No. 5,579,782 is incorporated by reference into this application as if set forth fully herein. The invention of this application is an improvement of our invention as disclosed in the previous application. The previous device employs a method to measure the internal impedance of the body using four electrodes. The impedance is measured between two points on the subject's body, specifically between the right hand and foot, between the hands, or between the feet. The subject makes contact with the electrodes by grasping them with his hands and exerting pressure on them with the bottoms of his feet.

As is shown in FIG. 14, this previous device for providing data as a guide to health management has a main unit 10, foot electrode unit 50 and cable 51, which connects foot electrode unit 50 to main unit 10. Main unit 10 includes console 11 and grips 12 and 13 for the left and right hands, which are formed integrally on either end of console 11. On the face of console 11 are power supply switch 14; key-switches 15, which are used to input a start command as well as the subject's physical characteristics, such as height and weight; and display 16, which displays the measurement results and advisory data. Display 16 is placed in the center of the area between left and right handgrips 12 and 13.

Left and right grips 12 and 13 are vertical cylinders on whose surfaces are provided electrodes 17 and 18, which apply a high-frequency signal, and electrodes 19 and 20, which measure the resistance of the body (by detecting voltage). Electrodes 17, 18, 19 and 20 are not shown in FIG. 14. They are electrically connected to circuits in console 11.

Foot electrode unit 50 consists of flat rectangular sheet 52, on which are two position guides, guide 53 for the left foot and guide 54 for the right foot. In each of these guides are two electrodes, 55 and 56, to apply a high-frequency signal, and two electrodes, 57 and 58, to measure the resistance of the body. At the front end of sheet 52, its top surface is partially covered by housing 59. Display 60, which is used to monitor the state of the measurement, is seated in this housing. Toward the front end of sheet 52 and between the foot position guides is an opening 61.

As can be seen in FIG. 16, sheet 52 is constructed of surface layer 62 and underlayer 63. Layers 62 and 63 can be composed of PVC, PET, polyethylene, or some similar substance. In the region corresponding to the arch of the foot in position guides 53 and 54 are elastic protrusions 64 and 65, on each of which are provided two of the aforesaid electrodes 55, 56, 57 and 58. FIG. 16 shows a cross section of the position guide for the right foot; the guide for the left foot has an identical construction. The electrodes have been placed on protrusions 64 and 65 so that all of them will make solid contact with the soles of the feet when the user places his feet in guides 53 and 54. Protrusions 64 and 65 are constructed of an elastic sheet made of a material such as silicon rubber. Housing 59 can be made of a material like ABS or PVC.

On either end of cable 51 are connectors 66 and 67, which allow it to connect main unit 10 and foot electrode unit 50 in such a way that it can easily be connected or disconnected. Let us consider how the device of this embodiment would be used to measure the impedance of the user's body. User M would stand as shown in FIG. 15, with both his feet in guides 53 and 54 on electrode unit 50. He would then grasp grip 12 on main unit 10 with his left hand and grip 13 with his right. Stretching his arms forward horizontally so as to hold unit 10 chest-high, he would begin making the measurements.

After the previous patent application for the aforesaid device to provide data as a guide to health management was filed, we became aware of the following problems through experience with the device:

(1) When the subject grasps the handgrips with both hands and stands with his feet on the foot electrodes, the pressure on the capillaries in the skin surface which is in contact with the electrodes will increase, and the state of the blood flow will temporarily change. This can be measured as a change in impedance (or resistance).

In concrete terms, when the pressure increases, the blood flow at the skin surface temporarily decreases and the subcutaneous resistance increases. The current flow becomes more dispersed, and the density of the current flowing into the main blood vessels temporarily decreases or increases. This will cause the voltage detected between the detector electrodes to rise or fall so that the resistance value will be lower than that measured in a stable state. The general characteristic of the settling time will be that the resistance value increases or decreases (See FIG. 12). The recovery time will vary among individuals, but stability is generally attained in five to ten seconds.

(2) If the subject has dry skin, the dry skin surface will cause the resistance value to be high. As described earlier, the path of the current flow becomes more dispersed, and the density of the current flow into the main blood vessels decreases. The detected voltage is observed to drop. The resistance value is lower than that measured in a stable state when there is moisture on the skin surface. The aforementioned recovery time will tend to be longer (See FIG. 13).

(3) When the impedance between the hands is measured while the subject is standing with arms outstretched at 90°, it must be measured for five to ten seconds in order to get beyond the period of fluctuation described above. If during this time there is variation in the position of the arms or the pressure of the hands on the electrodes, the measured value will fluctuate, resulting in a measurement error.

(4) When the impedance is measured while the subject is standing with his feet on the foot electrodes, he may change the position of his feet or shift his center of balance slightly as the measurement is being made. If the measurement site or the pressure varies, the measurement will fluctuate, and a measurement error will result.

(5) Once the start switch is actuated and measurement commences, there is a fixed period of time during which measurement must be completed. If in the initial stage of measurement a significant amount of time is used up in trying to achieve sufficient contact, there will be less time remaining in which to make the measurements. This will make it impossible to avoid the effects of the fluctuations described above.

SUMMARY OF THE INVENTION

A feature of this invention is to provide a device to measure impedance which is capable of highly accurate measurements and a device to provide data as a guide to health management which is highly reliable.

The device to measure impedance of this invention is equipped with electrodes to apply a high-frequency signal, electrodes to measure the resistance of the body, and a device which measures the impedance of the body using the signal obtained from the electrodes which measure resistance. This impedance measurement device is distinguished by the fact that it is equipped with a contact judging means which determines whether the subject has made good contact with the electrodes by determining whether the impedance value is within a prescribed range.

The impedance measurement device according to this invention recognizes as abnormal any measured impedance value which does not fall within a range defined by the possible impedance values of the human body. This results in high measurement accuracy.

The device to provide data as a guide to health management according to this invention has an impedance measurement device with electrodes to apply a high-frequency signal, electrodes to measure the resistance of the body, and a device which measures the impedance of the body using the signal obtained from the electrodes which measure resistance; and a device which outputs data concerning health management based on the impedance value measured by the measurement device. The aforesaid device to measure impedance is distinguished by the fact that it has a contact judging unit to determine, by judging whether the impedance value which is measured lies within a prescribed range, whether the electrodes to apply a high-frequency signal and electrodes to measure resistance are in proper contact with the body of the subject; and a automatic optimal impedance determination unit to measure an optimal impedance which, based on the result of this determination, measures the optimal impedance of the body and automatically determines the average value.

This device to provide data for health management determines whether the impedance value which is measured falls within a prescribed range. If it does, the device concludes that the subject's body is in good contact with the electrodes to apply a high-frequency signal and the electrodes to measure the resistance of the body. It then begins the processing to determine the optimal impedance value of the body.

BRIEF DESCRIPTION OF THE DRAWINGS

FIG. 10 illustrates the pattern displayed to represent impedance variability in the same preferred embodiment of a device to provide data as a guide to health management.

FIGS. 11(a)–11(d) show examples of display graphs representing impedance variability during measurement in the same preferred embodiment of a device to provide data as a guide to health management.

DETAILED DESCRIPTION OF THE INVENTION

Figure 1:
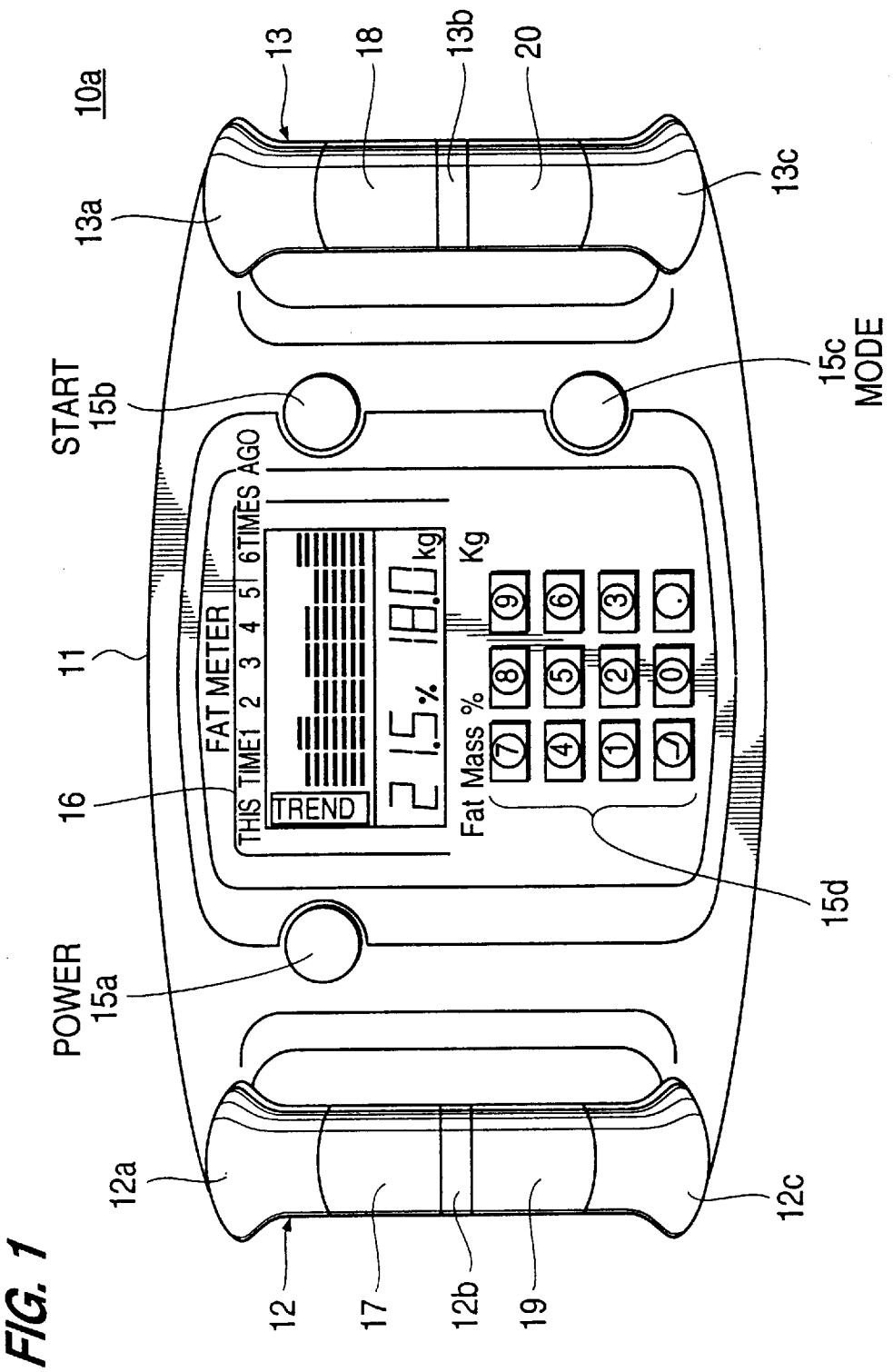
FIG. 1 shows the exterior of the main unit of a device to provide data as a guide to health management which is an preferred embodiment of this invention.

FIG. 1 shows the external appearance of the main unit of a device to provide data as a guide to health management which is an preferred embodiment of this invention. Main unit 10a is the component which has two perpendicular handgrips parallel to the long axis of the subject's body.

Main unit 10a has two vertical handgrips, 12 and 13, which are mounted in housing 11; display 16, an LCD or the like on the surface of housing 11 on which are displayed the health management data (visceral fat, lean mass, body fat ratio, moisture content, basal metabolic rate, and so on); power supply switch 15a; start switch 15b; mode switch 15c; and operating switches 15d. Within housing 11 are the circuits which are the electronic components of the CPU which calculates the internal impedance of the body and, based on the specific physical data of the subject (including height, weight, age and sex), data essential to health management.

Handgrips 12 and 13 are cylindrical. Annular electrodes 17 and 18, which apply a fixed current, are on their upper portion; and annular electrodes 19 and 20, which detect voltage, are on their lower portion. The two electrodes on each grip are separated by barrier segments (non-electrodes) 12b and 13b. On the upper and lower ends of the grips are positioning flanges 12a, 12c, 13a and 13c.

Figure 2:
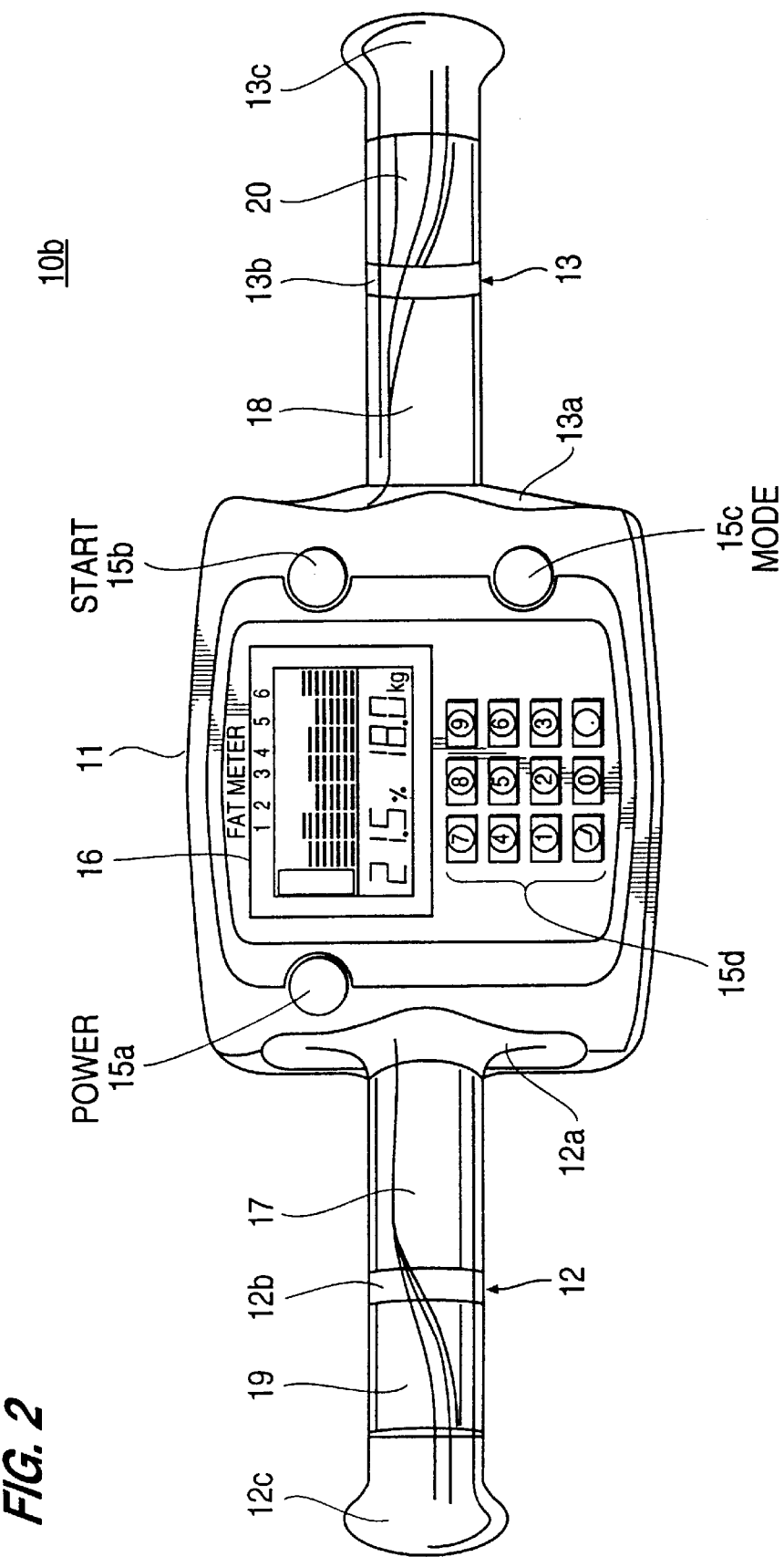
FIG. 2 shows the exterior of another device to provide data as a guide to health management which is an preferred embodiment of this invention.

Another configuration for the main unit is shown in FIG. 2. Here the device to provide data as a guide to health management has horizontal handgrips, which are grasped so that the hands are parallel to a line going through the subject's shoulders. Like the device in the preceding drawing, device 10b has two handgrips, 12 and 13, in this case projecting horizontally from housing 11; a display 16 on the surface of housing 11; and various operating switches, including power supply switch 15a, start switch 15b, mode switch 15c and numerical keys 15d.

Handgrips 12 and 13 in the embodiment of FIG. 2 are also cylindrical. Annular electrodes 17 and 18, which apply a fixed current, are on the portions of the grips closer to the display; annular electrodes 19 and 20, which detect voltage, are on the portions of the grips further from the display. Barrier segments 12b and 13b separate electrode 17 from electrode 19 and electrode 18 from electrode 20. On the inner and outer ends of the grips are positioning flanges 12a, 12c, 13a and 13c.

Figure 3A:
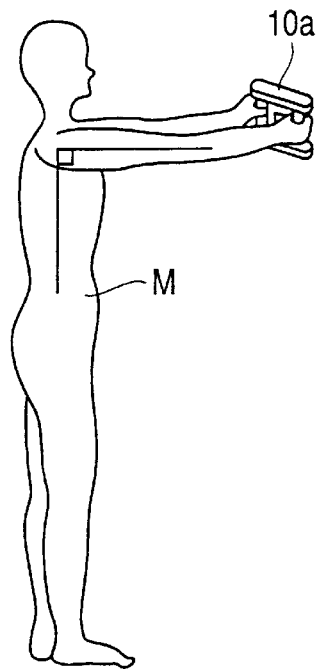
FIGS. 3(a) and 3(b) illustrate the use of the main unit of the device to provide data as a guide to health management which was shown in FIG. 1.
Figure 3B:
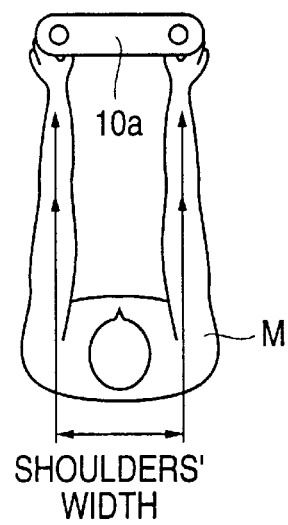
Figure 4A:
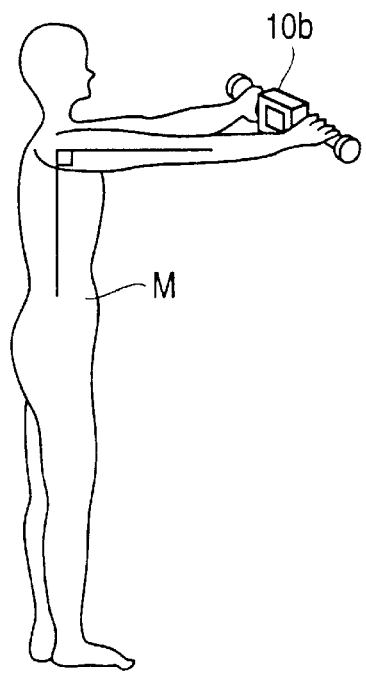
FIGS. 4(a) and 4(b) illustrate the use of the main unit of the device to provide data as a guide to health management which is shown in FIG. 2.
Figure 4B:
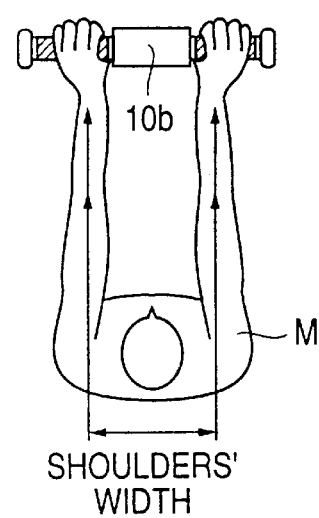

The use of the main unit 10a shown in FIG. 1 is illustrated in FIG. 3. Subject M extends his arms forward at a right angle to his body, keeping them a shoulders' width apart, and grasps handgrips 12 and 13. To use device 10b as depicted in FIG. 2, the subject grasps handgrips 12 and 13 as shown in FIG. 4.

Figure 5:
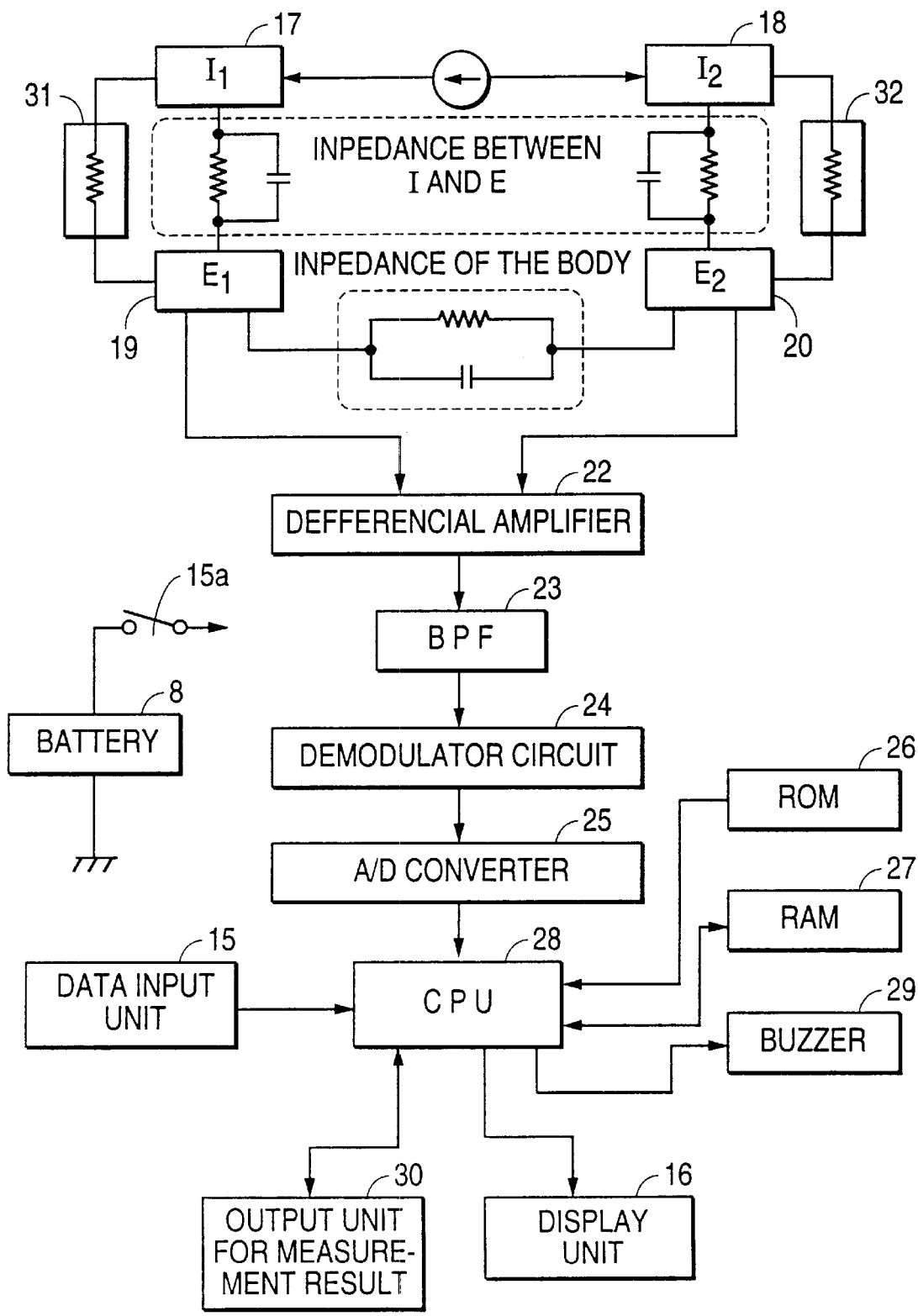
FIG. 5 is a block diagram of the circuits in the aforesaid device to provide data as a guide to health management.

FIG. 5 is a block diagram of the circuits in console 11 which are connected to electrodes 17 and 18 and to electrodes 19 and 20. The circuits inside the devices of this invention include, in addition to data input unit 15 and display unit 16, signal generator 21, which generates a signal of a fixed current at frequency $f_0$ ($10 \leq f_0 \leq 100$ Khz); differential amplifier 22, which receives a potential signal from electrodes 19 and 20; band pass filter 23, which cuts signals of frequencies other than $f_0$; circuit 24, which demodulates the high-frequency signal component; A/D converter 24, which digitizes the analog signal; ROM 26; RAM 27; CPU 28, which accepts the input of A/D converter 25 and the data from input unit 15, including the subject's height, weight, age and sex and the date, and executes the processing required to measure impedance and extract data pertaining to health management; warning buzzer 29; output unit 30, which transmits the measurement result to a printer or other device; battery 8, which serves as a power supply; resistor 31, which is connected between electrodes 17 and 19; and resistor 32, which is connected between electrodes 18 and 20.

To measure impedance using the devices discussed above, the subject grasps handgrips 12 and 13 with his hands. Signal generator 21 applies a signal of frequency $f_0$ to electrodes 17 and 18. This signal is transmitted through electrode 17, the subject's left hand, electrode 19, the subject's body (impedance), electrode 20, the subject's right hand, and electrode 18. The signal from electrodes 19 and 20 is amplified by differential amplifier 22 to obtain a signal representing potential difference.

Figure 6:
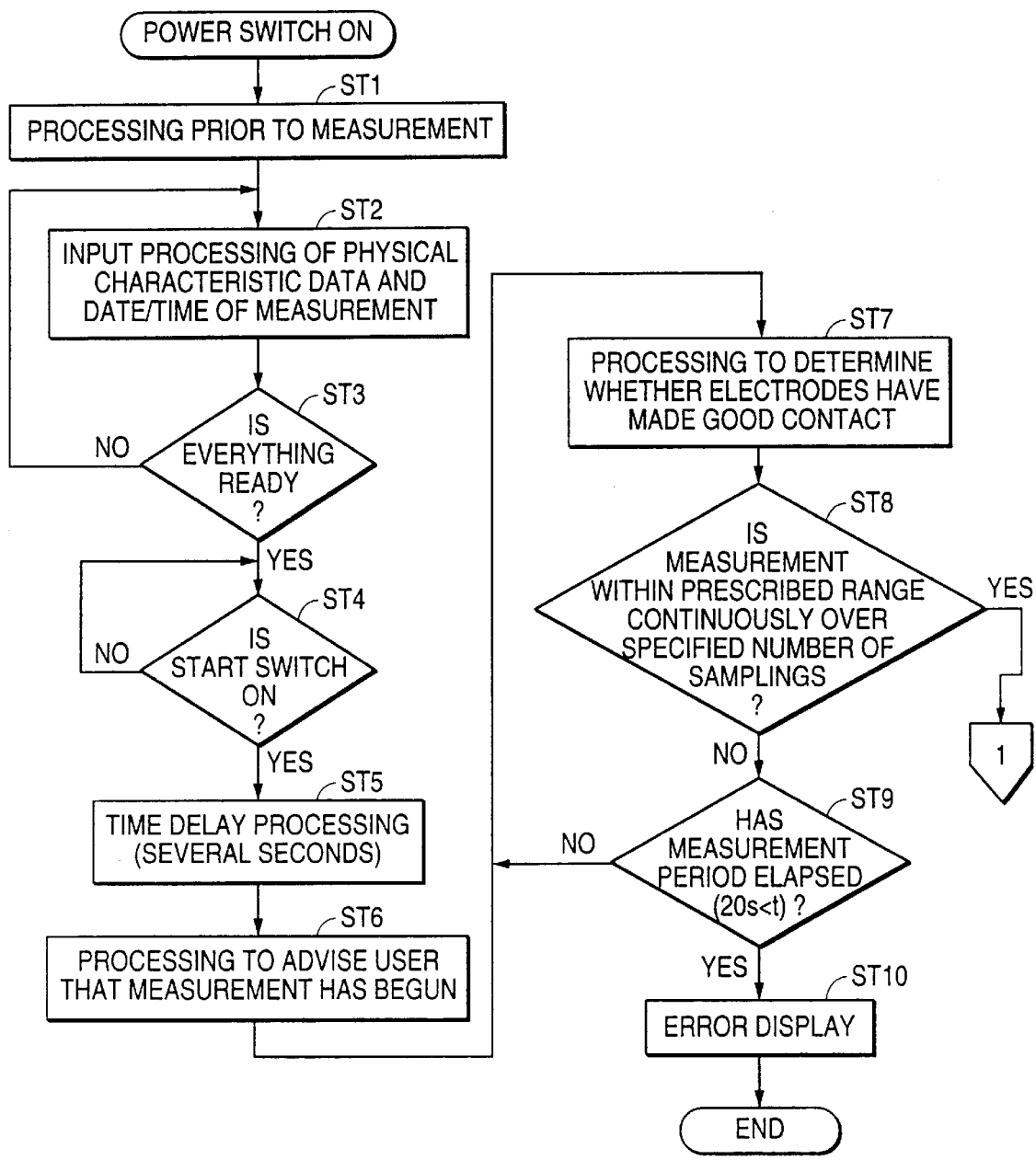
FIG. 6 is a flowchart elucidating the general operation of the same preferred embodiment of a device to provide data as a guide to health management.
Figure 7:
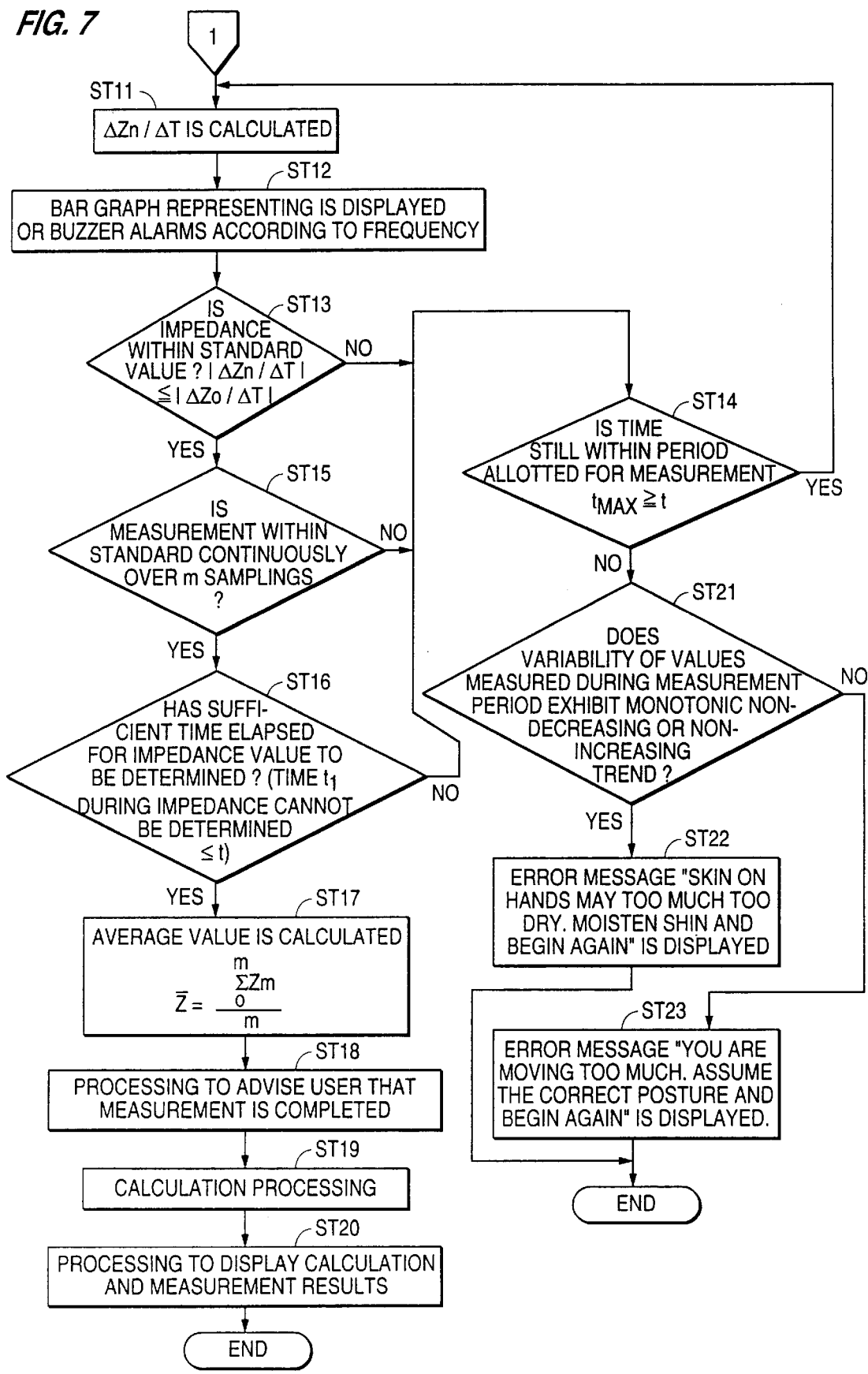
FIG. 7 is a flowchart elucidating the general operation of the same preferred embodiment of a device to provide data as a guide to health management, along with FIG. 6.

We shall next discuss the measurement operation executed by the device described above with reference to the flowchart in FIGS. 6 and 7. When power supply switch 15a is actuated, the preprocessing required for measurement is executed. This includes initializing the RAM and checking all circuit and display elements (Step 1). The subject then enters into data input unit 15 his or her characteristic physical data, including height, weight, age and sex, as well as the date and time (Step 2). The device stands by until data entry has been completed (Steps 2 and 3). Once all the data are entered, the device stands by until start switch 15b on input unit 15 is actuated (Step 4). At this point, the judgment in Step 3, "Is everything ready?", will be "yes", and the command "Press Start Switch" will appear on display 16. The display may also be used to cue the subject to begin key input. There is a time delay of several seconds after start switch 15b is actuated (Step 5), and then the fact that measurement has commenced is conveyed by buzzer 29 or display 16 (Step 6). The delay in Step 5 is set so as to furnish sufficient time for the subject to grasp handgrips 12 and 13 completely and properly after start switch 15b is actuated.

Figure 8:
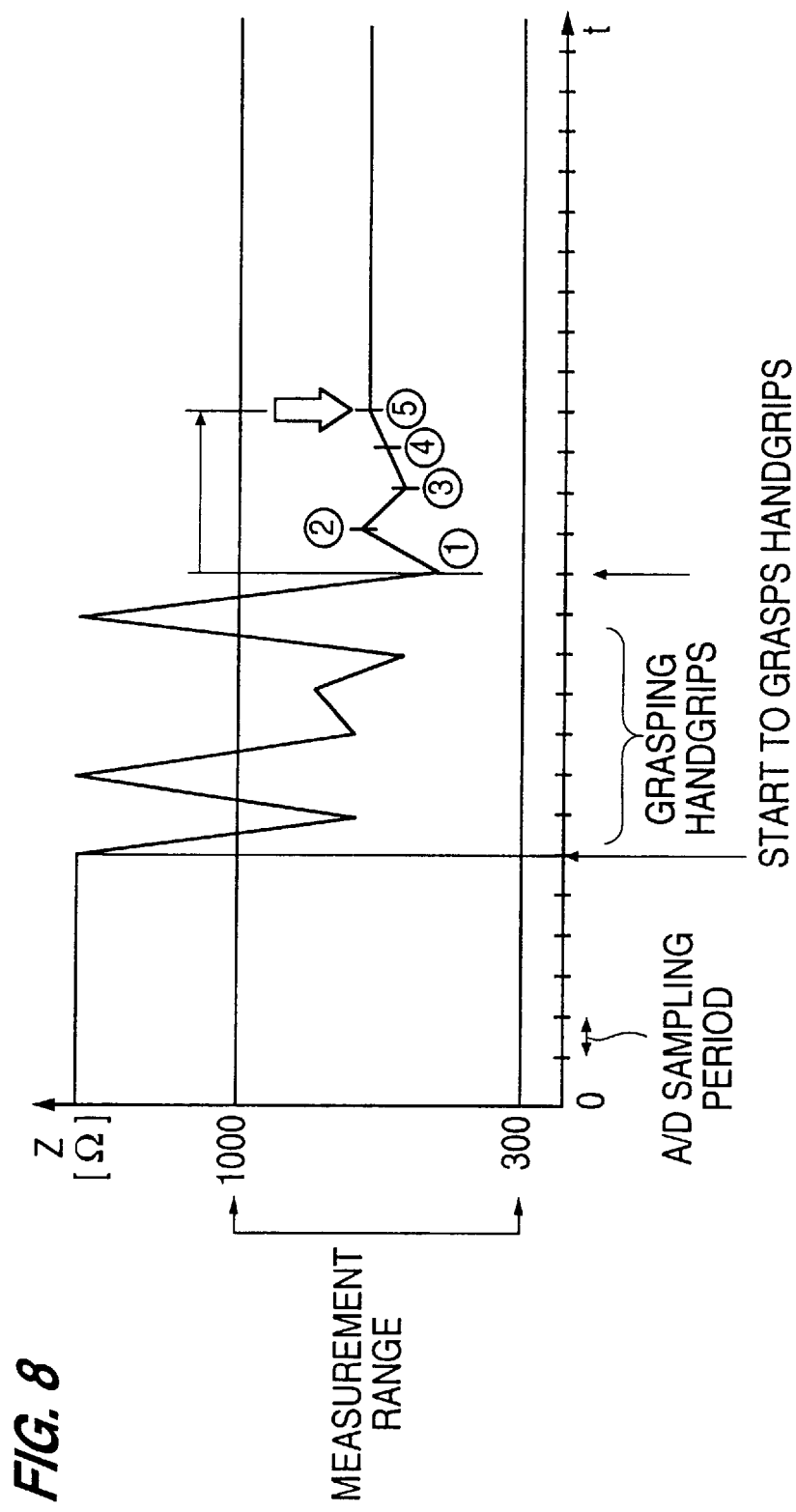
FIG. 8 is a time chart of the measured impedance which illustrates the processing to determine whether good contact has been made which is performed by the same embodiment of a device to provide data as a guide to health management.

The device proceeds at this point to the processing to determine whether a good contact has been made (Step 7). Once measurement has begun, a determination is made as to whether the measured impedance Z falls within a prescribed range, for example, between 300 and 1000 Ω (See FIG. 8). If it does not, the determination is that the hands are not making good contact with the electrodes, and if it does, the determination is that the hands are making good contact. Since the measurement will be unstable when the subject first grasps the handgrips, the earliest measured values will fluctuate wildly in and out of the range. For this reason, the judgment that good contact has been made (Step 8) will be rendered only when the measurement falls within the prescribed range five consecutive times, as shown by the arrow at time (5) in the graph of FIG. 8. If the measured impedance is not within the prescribed range, or if it does not remain in the range over five consecutive measurements, the judgment in Step 8 will be "no", and we will proceed to Step 9. Here a determination will be made as to whether a period longer than the allotted time (20 s <t) has elapsed since the processing to evaluate contact began. Until twenty seconds have elapsed, the device returns to Step 7 and repeats the processing to evaluate contact. If it is determined that the contact is imperfect after twenty seconds have elapsed, an error message is displayed (Step 10).

Figure 9:
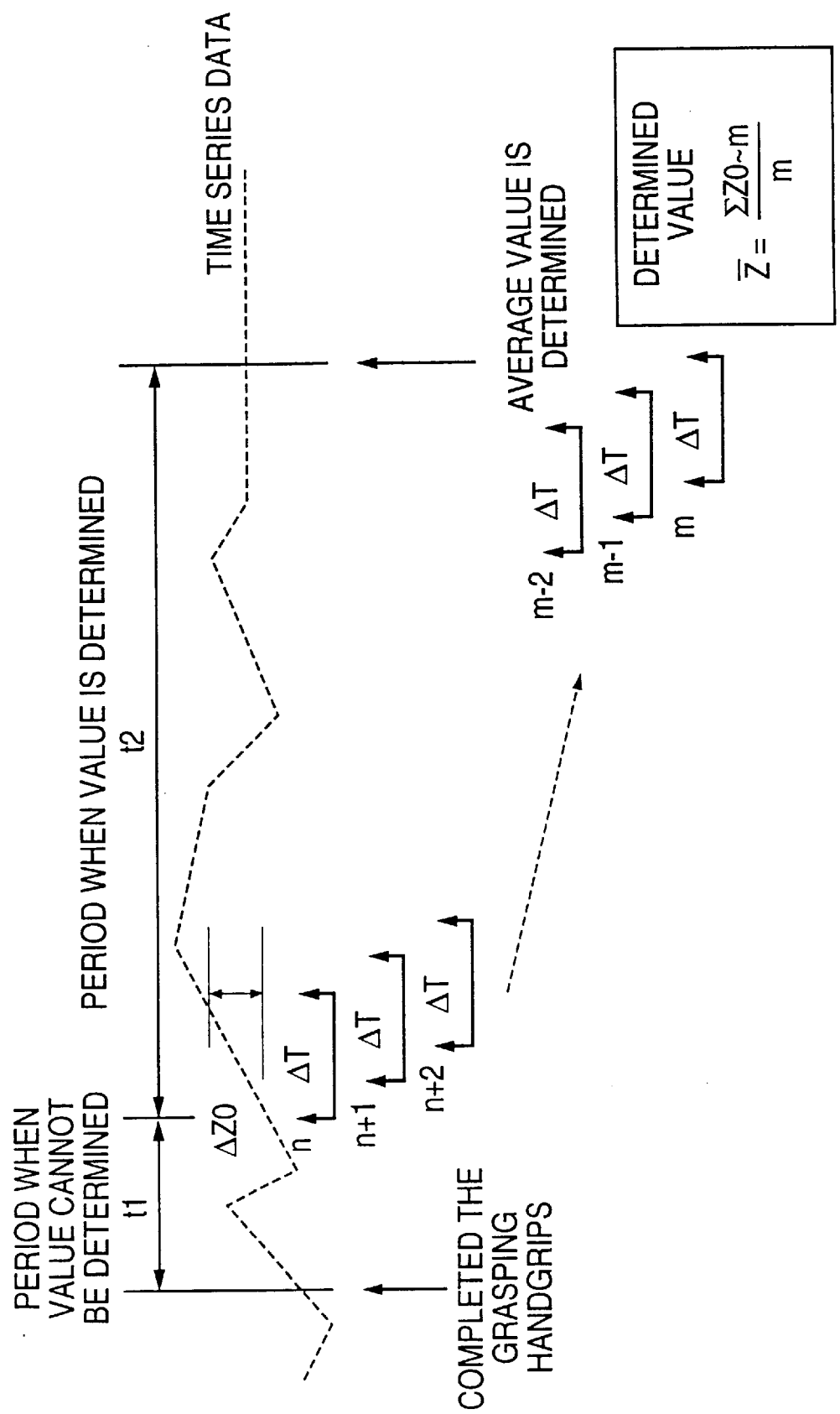
FIG. 9 is a time chart which illustrates the processing to automatically determine an impedance value which is performed by the same preferred embodiment of a device to provide data as a guide to health management.
Figure 12:
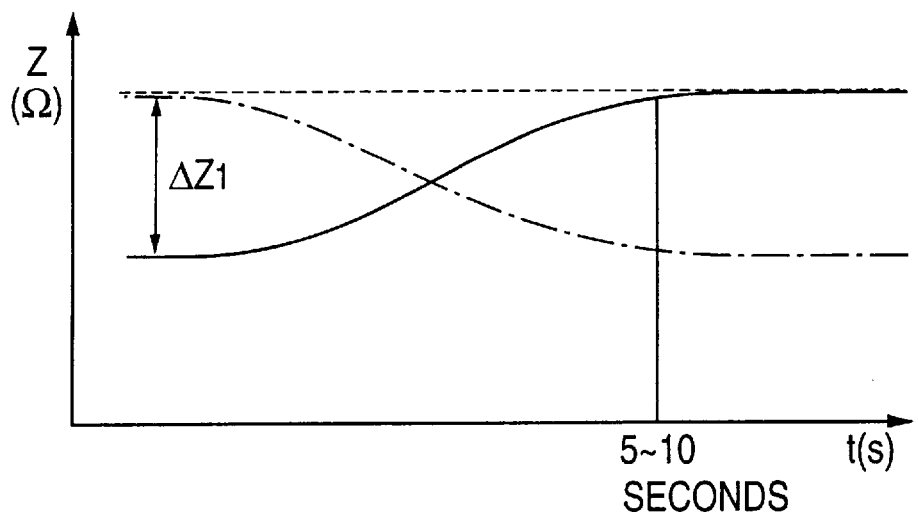
FIG. 12 shows impedance variability in an average person just after measurement has begun.
Figure 13:
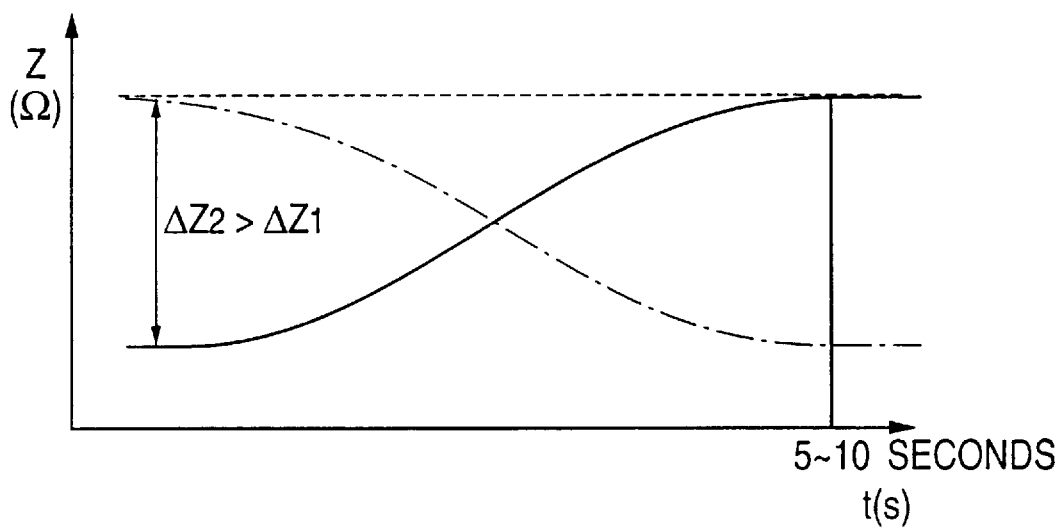
FIG. 13 shows impedance variability in a person with dry skin just after measurement has begun.
Figure 14:
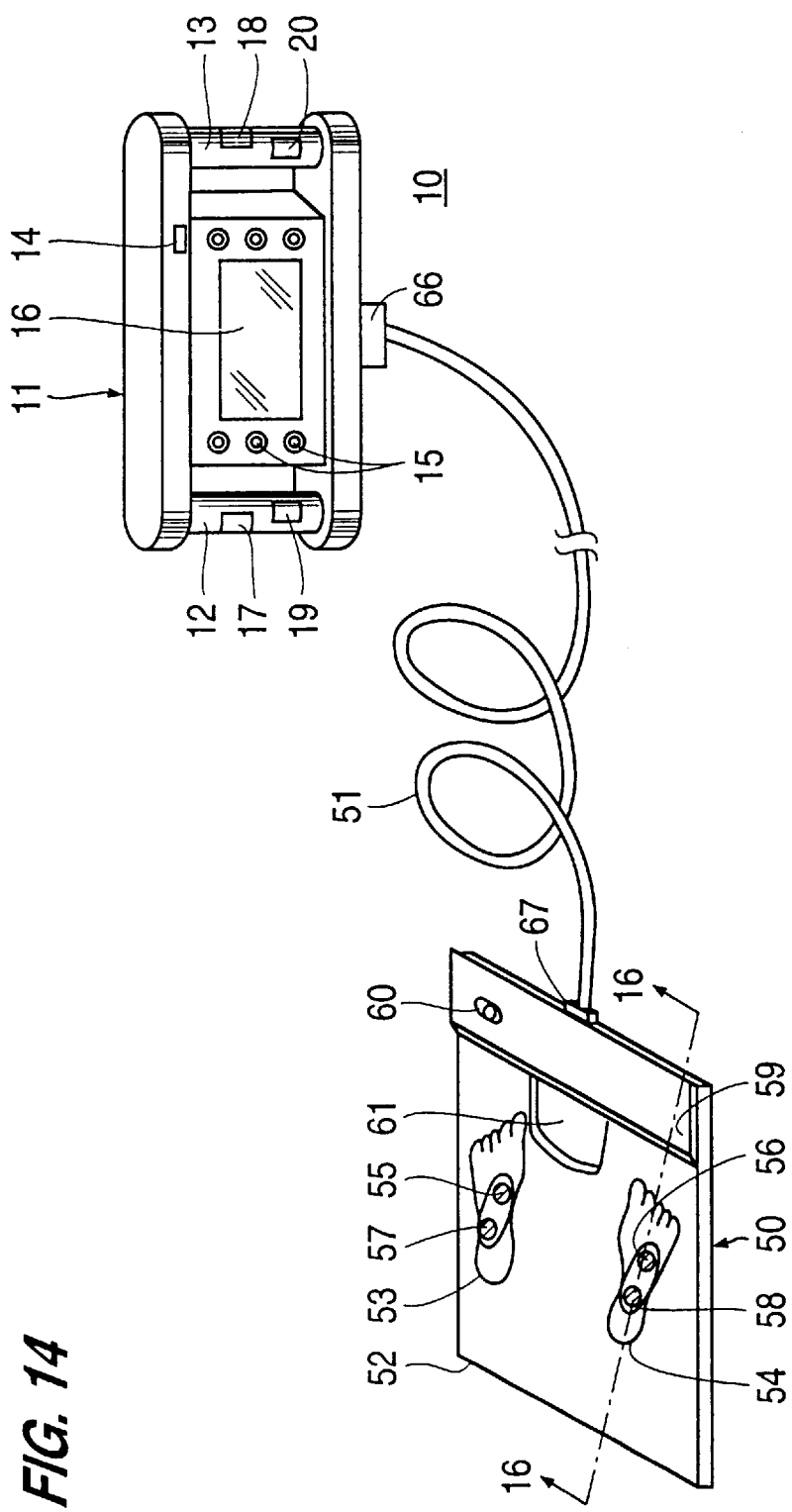
FIG. 14 shows the exterior of the device to provide data as a guide to health management which was disclosed in our previously patent application.
Figure 15:
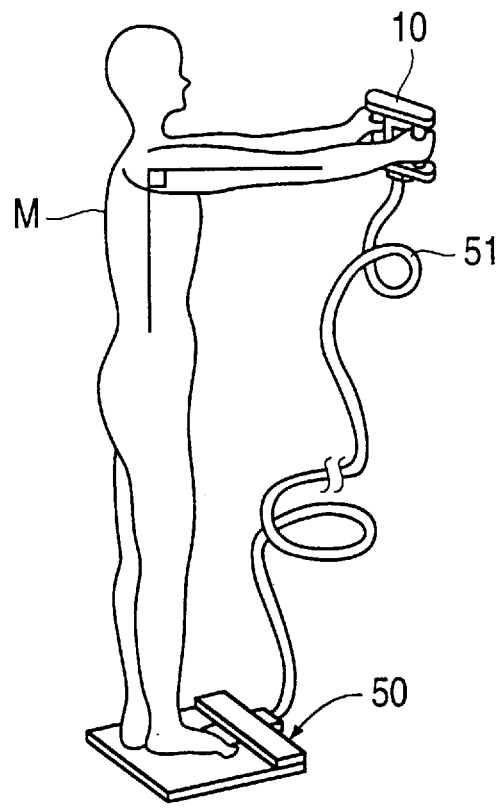
FIG. 15 illustrates the use of the device of FIG. 14 to provide data as a guide to health management.
Figure 16:
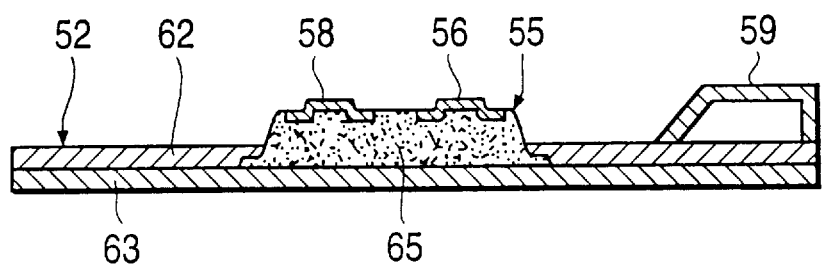
FIG. 16 is a cross section of the foot unit of the device shown in FIG. 15, taken along line A—A.

When it is determined in Step 8 that good contact has been made, we proceed to the processing beginning with Step 11, which automatically determines the average value. We shall discuss this processing with reference to FIG. 9. First, at sampling time $t_n$, we obtain $\Delta Z_n/\Delta T$, where $\Delta T$ is a specified period of time and $\Delta Z_n$ is the impedance as it has varied over $\Delta T$ (Step 11). A bar graph representing $\Delta Z_n/\Delta T$ is created on display 16, or buzzer 29 is used to indicate frequency (Step 12). The bar graph used to represent $\Delta Z$ on display 16 is shown in FIG. 10. The numerals on the graph indicate Ω/sec, and each segment represents 0.5 Ω. FIG. 11 shows a series of displays: FIG. 11(a) represents a $\Delta Z$ of more than 5 Ω/s, FIG. 11(b) a $\Delta Z$ of −2 Ω/s, and FIG. 11(c) a $\Delta Z$ of 1.5 Ω/s. When the impedance is within the standard value of ±1 Ω/s, as it is when $\Delta$=0.5 Ω/s, the segment will flash, as shown in FIG. 11(d).

Next, a determination is made as to whether the absolute value of $\Delta Z_n/\Delta T$ is within the standard value for $\Delta Z_o/\Delta T$ (0.5 Ω/s to 1 Ω/s) (Step 13). If it is not, we proceed to Step 14, where a determination is made as to whether any of the time allotted for measurement remains. If there is time remaining, we return to Step 11 and proceed to calculate $\Delta Z_n/\Delta T$ at the next sampling time.

If in Step 13 $\Delta Z_n/\Delta T$ is within the standard value, a determination is made as to whether it has been within the standard value continuously over m samplings (for example, m:3) (Step 15). If the impedance has not been within the standard value over m samplings, we return to Step 11 by way of Step 14. If the determination in Step 15 is "yes", a judgment is made as to whether a period of time has elapsed which is sufficient to determine a value, that is, whether the elapsed time is greater than $t_1$, the period during which the impedance value is not determinable (Step 16). If a period of time greater than $t_1$ has elapsed, we enter period $t_2$, during which processing will be executed to determine the impedance value. The average impedance value is calculated in accordance with Formula 1:

$$\text{Average Value } Z = \sum_{0}^{m} Z_m/m \text{ (Original).} \quad \text{Formula 1}$$

With this calculation, we settle on a value for the impedance (Step 17). Processing is then executed to apprise the user that measurement has been completed (Step 18). Various types of calculation processing are executed (Step 19), and finally the processing is performed to cause the calculation results and the measurement results to appear on display 16 (Step 20).

If in Step 16 not enough time has elapsed to determine an impedance value, we return to Step 11 by way of Step 14. If, while the elapsed time is still insufficient for a determination in Step 16, the measurement time limit is exceeded in Step 14, we proceed to Step 21, where a determination is made as to whether the variability of the measured value during the measurement period exhibited a monotonic non-increasing or nondecreasing trend. If the judgment in Step 21 is "yes", the error message "Skin may be too dry. Moisten skin surface and begin again" will appear on display 16 (Step 22). If the judgment in Step 21 is "no", the error message "You are moving too much. Assume the correct posture and begin again" will be displayed (Step 23).

FIGS. 17(a) and 18–27 illustrate handgrips 70A–70K, inclusive, which may be used in the devices of this invention in place of the handgrips depicted in FIGS. 1 and 2; in these figures the same reference numerals denote the same structures and functions. These handgrips may be fixed to the device or may be attached so that they can be rotated by the subject as necessary in order to provide firm contact between the handgrips and the hands of the subject.

Figure 17A:
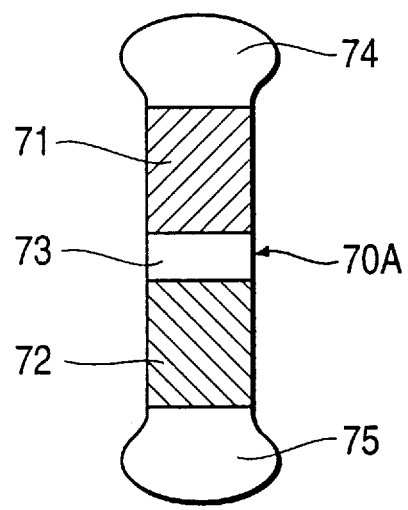
FIG. 17(a) shows the configuration of a handgrip according to this invention.
Figure 17B:
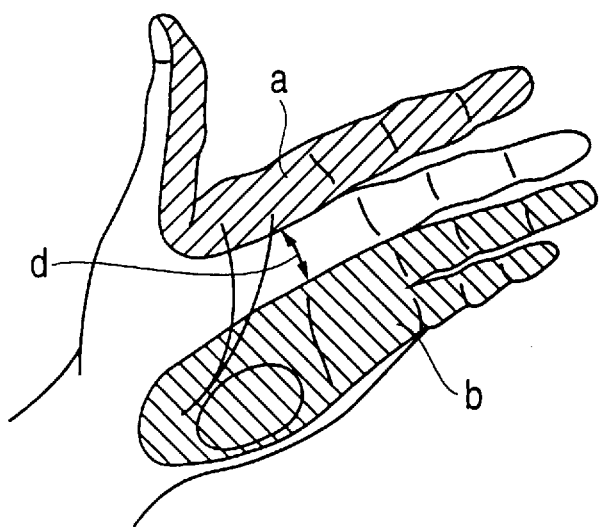
FIG. 17(b) shows the interaction of the handgrip of FIG. 17(a) with the left hand of a subject.

Handgrip 70A shown in FIG. 17(a) has a general dumbbell shape. Annular electrode 71 applies a fixed current like electrodes 17 and 18 in FIGS. 1 and 2; annular electrode 72 detects voltage like electrodes 19 and 20 in FIGS. 1 and 2; barrier segment 73 corresponds to barrier segments 12b and 13b in FIGS. 1 and 2; and upper end 74 and lower end 75 correspond to upper ends 12a, 12c and lower ends 12c, 13c in FIGS. 1 and 2. FIG. 17(b) shows how the left hand of a subject contacts the handgrip of FIG. 17(a) when the subject grips the handgrip of the device. Area a contacts annular electrode 71, while area b contacts annular electrode 72. Area d has a width, shown by the double-headed arrow in FIG. 17(b), which corresponds to the width of barrier segment 73.

Figure 18:
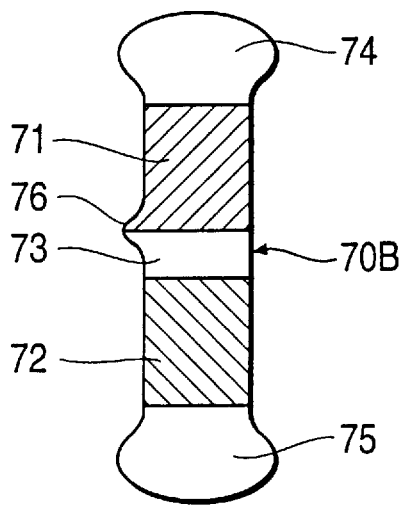
FIGS. 18–27 depict alternative handgrip configurations usable with the device of this invention.
Figure 19:
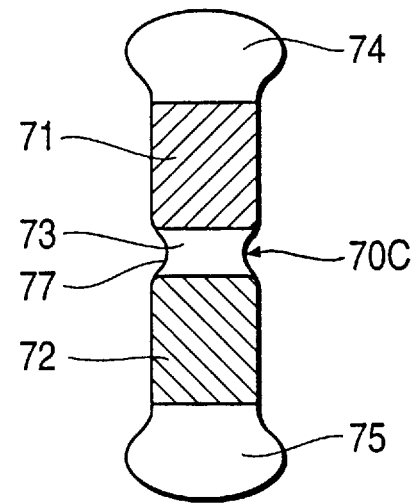
Figure 20:
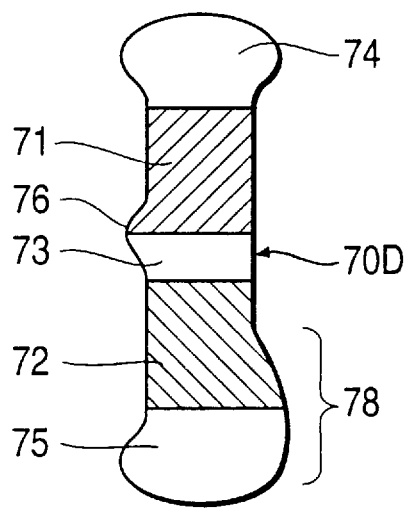
Figure 21:
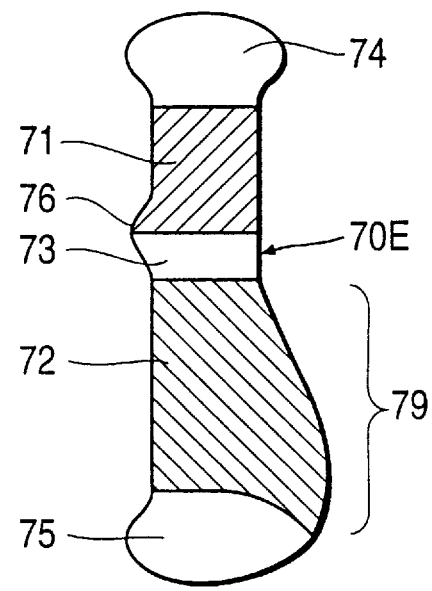
Figure 22:
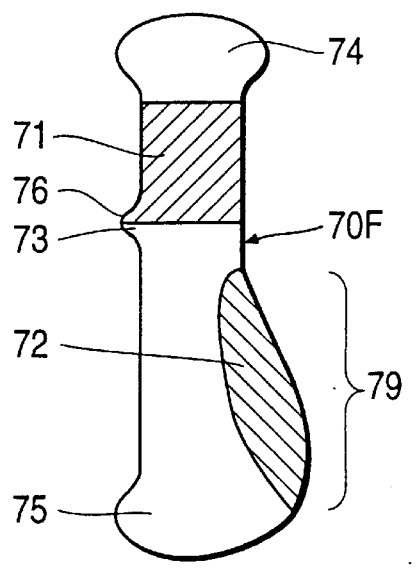
Figure 23:
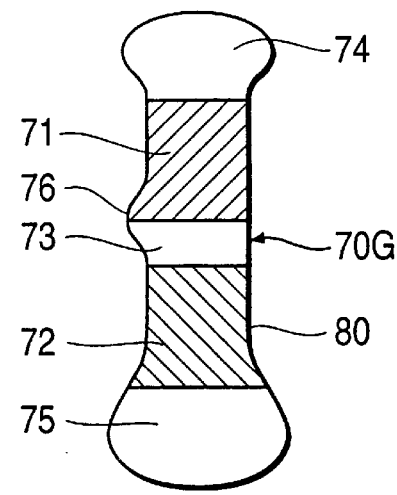
Figure 24:
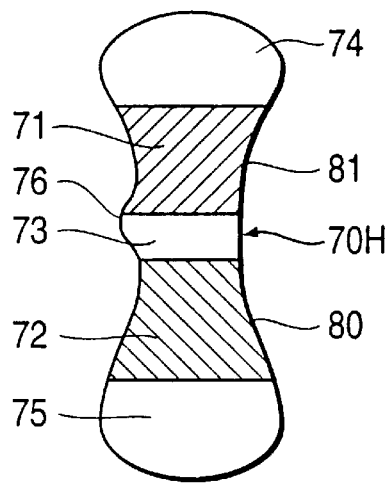

Handgrip 70B of FIG. 18 also includes a protrusion 76 which fits between the index and middle fingers of the subject. Handgrip 70C of FIG. 19 has an indentation or groove 77 forming the barrier segment 73 between annular electrodes 71 and 72. Handgrips 70D–70H of FIGS. 20–24 also have the protrusion 76 of FIG. 18; the electrodes 71 and 72 are widened and/or moved along the surface of the handgrip to provide a greater area of contact with the subject's hand; areas 78 and 79 show the greater area of contact with the palm of the subject available with handgrips 70D–70H with area b of FIG. 17(b). Reference numerals 80 and 81 on FIGS. 23 and 24 denote tapered areas for providing good contact between handgrips 70G and 70H and the palm of the subject.

Figure 25:
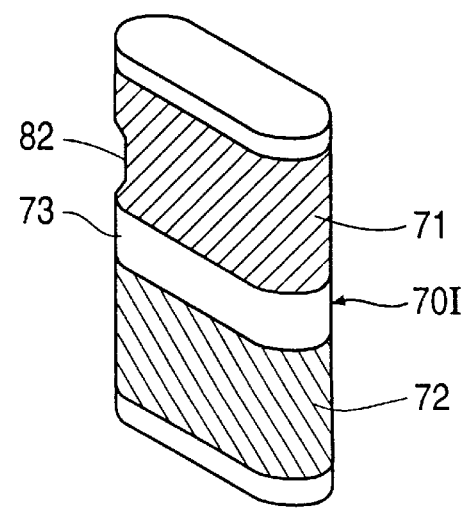
Figure 26:
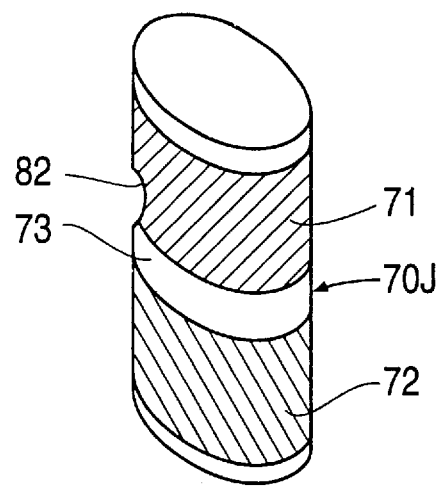

FIGS. 25 and 26 depict handgrips 70I and 70J of an oval cross section, in which indentation 82 acts as a guide for the index finger of the subject. Handgrip 70I has a "racetrack" shape, while handgrip 70J has a rounded oval shape.

Figure 27:
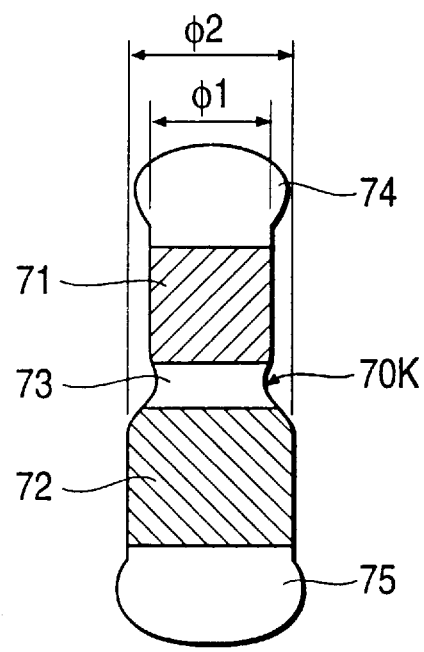

FIG. 27 depicts a handgrip 70K in which the upper portion of the handgrip over which electrode 71 lies has a diameter ø1 which is smaller than the diameter ø2 of the lower portion of the handgrip over which electrode 72 lies.

In the above examples we discussed the measurement of impedance between the hands. It is, of course, also possible for the device of this invention to measure the impedance between one hand and one foot or between the feet.

The invention of this application has a device to recognize abnormal conditions which detects insufficient contact with the electrodes or faulty contact or disconnection in a circuit, thereby enhancing the accuracy of the measurements. The invention of this application also includes a device to determine whether good contact has been made. This enables the devices of this invention to ascertain an optimal impedance value which is highly reliable. These devices also have a component which automatically executes the processing to determine the impedance value. This allows them to automatically determine an optimal impedance value which is highly reliable, making them ideally suited for personal use.

The invention of this application displays the likely source of an error based on what type of error it is, and it advises the user to begin again. This ensures that a highly reliable measurement can be made on the second try. The invention of this application also displays in real time the variability of a time series of measured values. This allows the device to automatically determine a value to operate effectively, and it allows the optimal impedance value to be determined with high reliability.

It will be understood that the appended claims describe the scope of the invention on which protection is sought in this application and that persons skilled in this art will be able to make modifications and improvements on the invention as disclosed herein which are within the scope and spirit of the appended claims. The specification of this application is illustrative of the invention and is not intended to restrict full coverage of the invention disclosed and claimed in this application.

What is claimed is:

1. A body fat detecting device, comprising:

a hand held element having first and second handgrips at respective ends of an axis thereof, said first and second handgrips being arrayed substantially parallel to each other in a direction substantially perpendicular to said axis;

a pair of first electrodes for inputting a high-frequency signal to a human body;

a pair of second electrodes for outputting said high frequency signal applied to said human body;

one of each of said first and second electrodes being mounted on said first handgrip and the other of each of said first and second electrodes being mounted on said second handgrip;

a signal generator configured to supply said high-frequency signal to said first electrodes;

measuring means for measuring an impedance of said human body using said output signal from said second electrodes, said determining means comprising condition judgment means for determining whether an abnormal condition exists or does not exist by determining whether said measured impedance is within a prescribed range; and a calculating device for calculating a fat mass of said human body based on said measured impedance.

2. A body fat detecting device according to claim 1, wherein said condition judgment means, once said measurement has commenced, confirms whether said pairs of first and second electrodes are making good contact with said human body by determining whether said measured impedance is in said prescribed range, performing said determination continuously for a specified number of times, at all times other than when said determination is being performed said condition judgment remaining in a stand-by state awaiting a commencement of measurement.

3. A body fat detecting device as claimed in claim 1, wherein said calculating unit outputs advice information including a probable reason for a problem and a request to perform measuring again according to a cause of said problem, if said problem is that a time series of said measured impedance exhibits a monotonic decreasing or non-decreasing trend, or if said time series exhibits variability above a specified value.

4. A body fat detecting device, comprising:

a hand held element having first and second handgrips at respective ends of an axis thereof, said first and second handgrips being arrayed substantially parallel to each other in a direction substantially perpendicular to said axis;

a pair of first electrodes for inputting a high-frequency signal to a human body;

a pair of second electrodes for outputting said high frequency signal applied to said human body;

one of each of said first and second electrodes being mounted on said first handgrip and the other of each of said first and second electrodes being mounted on said second handgrip;

a signal generator configured to supply said high-frequency signal to said first electrodes;

measuring means for measuring an impedance of said human body using said output signal from said second electrodes, said measuring means comprising condition judgment means for judging whether an abnormal condition exists or does not exist by determining whether said measured impedance is within a prescribed range and optimal impedance determining means for determining an optimal impedance after said condition judgment means judges that an abnormal condition does not exist; and a calculating device for calculating a fat mass of said human body based on said measured impedance.

5. A body fat detecting device as claimed in claim 4, wherein said optimal impedance determining means is configured for performing the functions of:

sampling a time series of values of said impedance of said human body;

calculating a variability of said impedance values over a specified sampling period or over multiple sampling periods;

comparing said variability with a normal impedance variability; and determining an average value which may be considered said optimal impedance of said human body when said variability is within said normal variability continuously over a prescribed number of measurements.

6. A body fat detecting device as claimed in claim 4, wherein said optimal impedance determining means holds said function of determining said average value until a prescribed period of time has elapsed after it has been determined that said first and second electrodes have made good contact with said human body.

7. A body fat detecting device according to claim 4, wherein said condition judgment means, once said measurement has commenced, confirms whether said pairs of first and second electrodes are making good contact with said human body by determining whether said measured impedance is in said prescribed range, performing said determination continuously for a specified number of times, at all times other than when said determination is being performed said condition judgment remaining in a stand-by state awaiting a commencement of measurement.

8. A body fat detecting device as claimed in claim 4, wherein said calculating device outputs an error message if said optimal impedance determining means does not determine said optimal impedance within a predetermined period of time.

9. A body fat detecting device as claimed in claim 4, wherein said calculating unit outputs advice information including a probable reason for a problem and a request to perform measuring again according to a cause of said problem, if said problem is that a time series of said measured impedance exhibits a monotonic decreasing or non-decreasing trend, or if said time series exhibits variability above a specified value.

10. A body fat detecting device as claimed in claim 9, wherein said calculating device outputs a variability of said time series of measured impedance in real time.

* * * * *